United States Patent [19]

Kumar

[11] Patent Number: 5,744,070
[45] Date of Patent: *Apr. 28, 1998

[54] PHOTOCHROMIC SUBSTITUTED NAPHTHOPYRAN COMPOUNDS

[75] Inventor: Anil Kumar, Pittsburgh, Pa.

[73] Assignee: Transitions Optical, Inc., Pinellas Park, Fla.

[*] Notice: The term of this patent shall not extend beyond the expiration date of Pat. No. 5,552,091.

[21] Appl. No.: 575,439

[22] Filed: Dec. 20, 1995

[51] Int. Cl.$^6$ .................. G02B 5/23; C07D 311/92
[52] U.S. Cl. .................. 252/586; 549/42; 549/383; 549/389; 549/457; 546/167; 546/273; 548/440; 548/454
[58] Field of Search .................. 252/586; 549/389, 549/383, 457, 42; 546/167, 273; 548/440, 454

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 252/300 |
| 4,215,010 | 7/1980 | Hovey et al. | 252/300 |
| 4,342,668 | 8/1982 | Hovey et al. | 252/300 |
| 4,563,458 | 1/1986 | Widding et al. | 252/586 |
| 4,637,698 | 1/1987 | Kwak et al. | 351/163 |
| 4,720,356 | 1/1988 | Chu | 252/586 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,931,221 | 6/1990 | Heller et al. | 252/586 |
| 5,066,818 | 11/1991 | Van Gemert | 549/389 |
| 5,200,116 | 4/1993 | Heller | 252/586 |
| 5,238,981 | 8/1993 | Knowles | 524/110 |
| 5,244,602 | 9/1993 | Van Gemert | 252/589 |
| 5,274,132 | 12/1993 | Van Gemert | 549/389 |
| 5,369,158 | 11/1994 | Knowles | 524/110 |
| 5,384,077 | 1/1995 | Knowles | 252/586 |
| 5,395,567 | 3/1995 | Van Gemert et al. | 252/586 |
| 5,405,958 | 4/1995 | Van Gemert et al. | 252/586 |
| 5,429,774 | 7/1995 | Kumar | 252/586 |
| 5,451,344 | 9/1995 | Knowles et al. | 252/586 |
| 5,458,814 | 10/1995 | Kumar et al. | 252/586 |
| 5,458,815 | 10/1995 | Knowles | 252/586 |
| 5,466,398 | 11/1995 | Van Gemert et al. | 252/586 |
| 5,520,853 | 5/1996 | Rickwood et al. | 252/586 |
| 5,543,533 | 8/1996 | Allegrini et al. | 549/389 |
| 5,552,091 | 9/1996 | Kumar | 252/586 |
| 5,573,712 | 11/1996 | Kumar et al. | 252/586 |
| 5,578,252 | 11/1996 | Van Gemert et al. | 252/586 |
| 5,585,042 | 12/1996 | Knowles | 252/586 |

FOREIGN PATENT DOCUMENTS

| | | |
|---|---|---|
| 246114 | 5/1987 | European Pat. Off. |
| 250193 | 6/1987 | European Pat. Off. |
| 294056 | 12/1988 | European Pat. Off. |
| 62-195383 | 8/1987 | Japan |
| 02/69471 | 3/1990 | Japan |
| 7-41758 | 2/1995 | Japan |
| 7-48363 | 2/1995 | Japan |
| 7-48566 | 2/1995 | Japan |
| 7-48567 | 2/1995 | Japan |
| WO94/22850 | 10/1994 | WIPO |
| WO95/05371 | 2/1995 | WIPO |

OTHER PUBLICATIONS

*Friedel–Crafts and Related Reactions*, George A. Olah, Interscience Publishers, vol. 3, Chap. XXXI, pp. 1–8, 1964.

"Regioselective Friedel Crafts Acylation of 1,2,3,4–Tetrahydroquinoline and Related Nitrogen Heterocycles: Effects of NH Protective Groups and Ring Size", Ishihara, Y., et al, J. Chem. Soc., Perkin Trans. 1, pp. 3401–3406, 1992.

*Organic Synthesis*, vol. 32, John Wiley and Sons, Inc., pp. 72–76 (1952).

*Primary Examiner*—Philip Tucker
*Attorney, Agent, or Firm*—Frank P. Mallak; Irwin M. Stein

[57] ABSTRACT

Described are novel reversible photochromic naphthopyran compounds, examples of which are 3H-naphtho[2,1-b] pyrans having an acyl or aroyl oxy-bearing substituent at the number 6 carbon atom and certain substituents at the 3-position of the pyran ring. Certain substituents may also be present at the number 5, 7, 8, 9 or 10 carbon atom of the naphthopyran. These compounds may be represented by the following graphic formula:

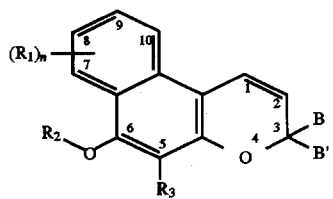

Also described are polymeric organic host materials that contain or that are coated with such compounds. Optically clear articles such as ophthalmic lenses or other plastic transparencies that incorporate the novel naphthopyran compounds or combinations thereof with complementary photochromic compounds, e.g., certain other naphthopyrans, benzopyrans, and spiro(indoline)type compounds, are also described.

20 Claims, No Drawings

PHOTOCHROMIC SUBSTITUTED NAPHTHOPYRAN COMPOUNDS

DESCRIPTION OF THE INVENTION

The present invention relates to certain novel naphthopyran compounds. More particularly, this invention relates to novel photochromic naphthopyran compounds and to compositions and articles containing such novel naphthopyran compounds. When exposed to light radiation involving ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of these compounds with visible light or upon raising the temperature to above about 0° C. is reported to reverse the coloration to a colorless state. WO 94/22850 and 95/05371 (Rickwood) describe naphthopyrans having various substituents at the 6-position of the naphtho-portion of the naphthopyran as useful photochromic materials in lenses, e.g. sunglasses, and photochromic transparencies.

The present invention relates to novel 3H-naphtho[2,1-b] pyran compounds having certain substituents at the number 3 and 6 carbon atoms. Certain substituents may also be present at the number 5, 7, 8, 9 or 10 carbon atom of the naphthopyran. Transparent photochromic articles made of a polymeric organic host material incorporated with these compounds have less residual color and higher luminous transmittance in the unactivated state than photochromic articles incorporated with corresponding compounds having different substituents at the number 6 carbon atom on the naphtho portion of the naphthopyran.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

Photochromic compounds useful in optical applications, such as conventional ophthalmic lenses, are those which possess (a) a high quantum efficiency for coloring in the near ultraviolet, (b) a low quantum yield for bleaching with white light, and (c) a relatively fast thermal fade at ambient temperature but not so rapid a thermal fade rate that the combination of white light bleaching and thermal fade prevent coloring by the ultraviolet component of strong sunlight. In addition, the aforesaid properties are desirably retained in conventional rigid synthetic plastic materials customarily used for ophthalmic and plano lenses when such materials have applied to or incorporated therein such photochromic compounds.

Another factor regarding the selection of potential photochromic compounds for optical applications is their residual color, i.e., color of the unactivated photochromic compound, in conventional plastic materials customarily used for ophthalmic and plano lenses. A related factor is the effect of the unactivated photochromic compound on the luminous transmittance of the plastic material. Ideally, photochromic compounds in the unactivated state contribute minimal color to the photochromic article and minimally reduce the luminous transmittance of the photochromic article.

The compounds of the present invention may be described as 3H-naphtho[2,1-b]pyrans that are substituted with an acyl or aroyl oxy-bearing substituent at the number 6 carbon atom and certain substituents may also be present at the number 5, 7, 8, 9 or 10 carbon atom of the naphthopyran. In addition, these compounds have certain substituents at the 3-position of the pyran ring. These naphthopyran compounds may be represented by the following graphic formula I:

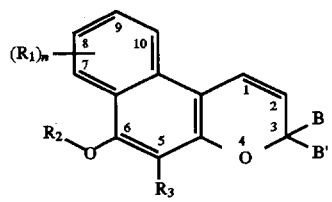

$R_1$ in graphic formula I may be a $C_1$-$C_6$ alkyl, e.g., methyl, ethyl, propyl, n-butyl, iso-butyl, n-amyl, iso-amyl, hexyl, etc., $C_5$-$C_7$ cycloalkyl, chloro, fluoro, the group, —$OR_4$, or the group, —$C(O)W$, W being $C_1$-$C_6$ alkyl, —$OR_5$ or —$N(R_6)R_7$, wherein $R_4$ is hydrogen, allyl, $C_1$-$C_6$ alkyl, phenyl, $C_1$-$C_6$ monoalkyl substituted phenyl, e.g., tolyl, cumenyl, etc., $C_1$-$C_6$ monoalkoxy substituted phenyl, e.g., anisyl, ethoxyphenyl, etc., phenyl($C_1$-$C_3$)alkyl, e.g., benzyl, phenethyl, 3-phenylpropyl, etc., $C_1$-$C_6$ monoalkyl substituted phenyl($C_1$-$C_3$)alkyl, $C_1$-$C_6$ monoalkoxy substituted phenyl($C_1$-$C_3$)alkyl, $C_1$-$C_6$ alkoxy($C_2$-$C_4$)alkyl, $C_1$-$C_6$ monofluoroalkyl, $C_1$-$C_6$ monochloroalkyl, $C_1$-$C_6$ alkylcarbonyl, monochloro($C_1$-$C_6$)alkylcarbonyl, monofluoro($C_1$-$C_6$)alkylcarbonyl, $C_1$-$C_6$ monoalkylaminocarbonyl, mono- or di-substituted arylcarbonyl, the aryl group being phenyl or naphthyl. $R_5$ may be hydrogen, allyl, $C_1$-$C_6$ alkyl, phenyl, $C_1$-$C_6$ monoalkyl substituted phenyl, $C_1$-$C_6$ monoalkoxy substituted phenyl, phenyl($C_1$-$C_3$)alkyl, $C_1$-$C_6$ monoalkyl substituted phenyl($C_1$-$C_3$)alkyl, $C_1$-$C_6$ monoalkoxy substituted phenyl($C_1$-$C_3$)alkyl, $C_1$-$C_6$ alkoxy($C_2$-$C_4$)alkyl, $C_1$-$C_6$ monofluoroalkyl or $C_1$-$C_6$ monochloroalkyl. $R_6$ and $R_7$ may each be selected from the group consisting of hydrogen, $C_1$-$C_6$ alkyl, $C_5$-$C_7$ cycloalkyl, phenyl, mono-substituted phenyl, and di-substituted phenyl, or $R_6$ and $R_7$ may together with the attached nitrogen atom form an unsubstituted, mono-substituted or di-substituted heterocyclic ring selected from the group consisting of indolinyl, morpholino, piperidino, 1-pyrrolidyl, 1-pyrrolinyl, 1-imidazolidyl, 2-imidazolin-1-yl, 2-pyrazolidyl and 1-piperazinyl. The aforementioned phenyl, naphthyl and heterocyclic ring substituents being $C_1$-$C_6$ alkyl or $C_1$-$C_6$ alkoxy, and n is the integer 0, 1, 2 or 3.

Preferably, $R_1$ is a $C_1$-$C_4$ alkyl, or the group, —$OR_4$, wherein $R_4$ is hydrogen, $C_1$-$C_4$ alkyl, phenyl, $C_1$-$C_4$ monoalkyl substituted phenyl, $C_1$-$C_4$ monoalkoxy substituted phenyl, phenyl($C_1$-$C_3$)alkyl, $C_1$-$C_4$ monoalkyl substituted phenyl($C_1$-$C_3$)alkyl, $C_1$-$C_4$ monoalkoxy substituted phenyl($C_1$-$C_3$)alkyl, $C_1$-$C_4$ alkoxy($C_2$-$C_4$)alkyl, $C_1$-$C_4$ monofluoroalkyl, $C_1$-$C_4$ monochloroalkyl or $C_1$-$C_4$ alkylcarbonyl, and n is the integer 0, 1 or 2.

More preferably, $R_1$ is a $C_1$-$C_3$ alkyl, or the group, —$OR_4$, wherein $R_4$ is hydrogen, $C_1$-$C_3$ alkyl, phenyl, $C_1$-$C_3$ monoalkyl substituted phenyl, $C_1$-$C_3$ monoalkoxy substituted phenyl, $C_1$-$C_3$ alkoxy($C_2$-$C_4$)alkyl, $C_1$-$C_3$ monofluoroalkyl or $C_1$-$C_3$ alkylcarbonyl, and n is the integer 0, 1 or 2. Most preferably, $R_1$ is a $C_1$-$C_2$ alkyl or the group, —$OR_4$, wherein $R_4$ is a $C_1$-$C_2$ alkyl, and n is the integer 0 or 1.

In graphic formula I, $R_2$ may be hydrogen, or the group, —C(O)X, wherein X may be hydrogen, $C_1$-$C_6$ alkyl, $C_1$-$C_6$ alkoxy, $C_1$-$C_6$ monofluoroalkyl, $C_1$-$C_6$ monochloroalkyl, phenyl($C_1$-$C_3$)alkyl, mono($C_1$-$C_6$)alkyl substituted phenyl ($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ alkylamino, allyl, or the unsubstituted, mono-substituted or di-substituted member selected from the group consisting of phenyl, naphthyl, phenoxy and phenylamino, said group substituents being $C_1$-$C_6$ alkyl or $C_1$-$C_6$ alkoxy.

Preferably, $R_2$ is hydrogen, or the group, —C(O)X, wherein X is hydrogen, $C_1$-$C_4$ alkyl, $C_1$-$C_4$ alkoxy, $C_1$-$C_4$ monofluoroalkyl, $C_1$-$C_4$ monochloroalkyl, phenyl($C_1$-$C_3$)alkyl, mono($C_1$-$C_4$)alkyl substituted phenyl($C_1$-$C_3$)alkyl, mono($C_1$-$C_4$)alkoxy substituted phenyl($C_1$-$C_3$)alkyl, $C_1$-$C_4$ alkoxy($C_2$-$C_4$)alkyl, $C_3$-$C_7$ cycloalkyl, phenyl, mono($C_1$-$C_4$)alkyl substituted phenyl, mono($C_1$-$C_4$)alkoxy substituted phenyl, phenoxy, mono($C_1$-$C_4$)alkyl substituted phenoxy, mono($C_1$-$C_4$)alkoxy substituted phenoxy, $C_1$-$C_4$ alkylamino, phenylamino, mono($C_1$-$C_4$)alkyl substituted phenylamino, or mono($C_1$-$C_4$)alkoxy substituted phenylamino.

More preferably, $R_2$ is hydrogen, or the group, C(O)X, wherein X is hydrogen, $C_1$-$C_3$ alkyl, $C_1$-$C_3$ alkoxy, $C_1$-$C_3$ monofluoroalkyl, phenyl, mono($C_1$-$C_3$)alkyl substituted phenyl, mono($C_1$-$C_3$)alkoxy substituted phenyl, phenoxy, mono($C_1$-$C_3$)alkyl substituted phenoxy, mono($C_1$-$C_3$) alkoxy substituted phenoxy, $C_1$-$C_3$ alkylamino, phenylamino, mono ($C_1$-$C_3$) alkyl substituted phenylamino, or mono ($C_1$-$C_3$) alkoxy substituted phenylamino. Most preferably, $R_2$ is hydrogen or the group, —C(O)X, wherein X is $C_1$-$C_2$ alkyl, $C_1$-$C_2$ alkoxy or $C_1$-$C_2$ alkylamino.

$R_3$ in graphic formula I may be hydrogen or $C_1$-$C_6$ alkyl. Preferably, $R_3$ is hydrogen or $C_1$-$C_4$ alkyl, more preferably, hydrogen or $C_1$-$C_3$ alkyl, and most preferably, hydrogen.

In graphic formula I, B and B' may each be selected from the group consisting of: (i) the unsubstituted, mono-, di- and tri-substituted aryl groups phenyl and naphthyl; (ii) the unsubstituted, mono- and di-substituted heterocyclic aromatic groups pyridyl, furanyl, benzofuran-2-yl, benzofuran3-yl, thienyl, benzothien-2-yl, benzothien-3-yl, dibenzothienyl, dibenzofuranyl and carbazolyl, the aryl and heterocyclic group substituents being selected from the group consisting of hydroxy, amino, $C_1$-$C_6$ monoalkylamino, $C_1$-$C_6$ dialkylamino, i.e., di-($C_1$-$C_6$) alkylamino, morpholino, piperidino, 1-indolinyl, pyrrolidyl, 1-imidazolidyl, 2imidazolin-1-yl, 2-pyrazolidyl, pyrazolinyl, 1-piperazinyl, $C_1$-$C_6$ alkyl, $C_1$-$C_6$ haloalkyl, $C_1$-$C_6$ alkoxy, mono($C_1$-$C_6$)alkoxy($C_1$-$C_4$)alkyl, acryloxy, methacryloxy and halogen, wherein each of the described halogen or (halo) group may be fluoro or chloro; (iii) the groups represented by the following graphic formulae II A and II B:

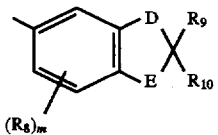

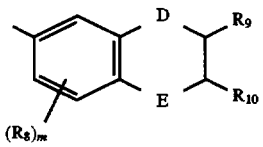

wherein D may be carbon or oxygen and E may be oxygen or substituted nitrogen, provided that when E is substituted nitrogen, D is carbon, said nitrogen substituent being selected from the group consisting of hydrogen, $C_1$-$C_6$ alkyl and $C_2$-$C_6$ acyl; each $R_8$ may be $C_1$-$C_6$ alkyl, $C_1$-$C_6$ alkoxy, hydroxy or halogen, wherein the halogen may be chloro or fluoro; $R_9$ and $R_{10}$ may each be hydrogen or $C_1$-$C_6$ alkyl; and m may be the integer 0, 1 or 2; (iv) $C_1$-$C_6$ alkyl, $C_1$-$C_6$ haloalkyl, $C_1$-$C_6$ alkoxy($C_1$-$C_4$)alkyl, $C_3$-$C_6$ cycloalkyl, mono($C_1$-$C_6$)alkoxy($C_3$-$C_6$)cycloalkyl, mono($C_1$-$C_6$)alkyl ($C_3$-$C_6$)cycloalkyl, and halo($C_3$-$C_6$)cycloalkyl, each of said halo groups being fluoro or chloro; and (v) the group represented by the following graphic formula II C:

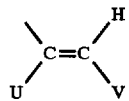

wherein U may be hydrogen or $C_1$-$C_4$ alkyl, and V may be selected from the unsubstituted, mono- and di-substituted members of the group consisting of naphthyl, phenyl, furanyl and thienyl, wherein the substituents for each member of said group are $C_1$-$C_4$ alkyl, $C_1$-$C_4$ alkoxy, fluoro or chloro; or (vi) B and B' taken together form an unsubstituted, mono- or di-substituted fluoren-9-ylidene or form a member selected from the group consisting of saturated $C_3$-$C_{12}$ spiro-monocyclic hydrocarbon rings, e.g., cyclopropylidene, cyclobutylidene, cyclopentylidene, cyclohexylidene, cycloheptylidene; cyclooctylidene, cyclononylidene, cyclodecylidene, cycloundecylidene and cyclododecylidene, saturated $C_7$-$C_{12}$ spiro-bicyclic hydrocarbon rings, e.g., bicyclo[2.2.1]heptylidene, i.e., norbornylidene, 1,7,7trimethyl bicyclo[2.2.1]heptylidene, i.e., bornylidene, bicyclo[3.2.1]octylidene, bicyclo[3.3.1]nonan-9-ylidene and bicyclo[4.3.2]undecane, and saturated $C_7$-$C_{12}$ spiro-tricyclic hydrocarbon rings, e.g., tricyclo [2.2.1.0$^{2,6}$]heptylidene, tricyclo[5.3.1.1$^{2,6}$]dodecylidene and tricyclo[3.3.1.1$^{3,7}$]-decylidene, i.e., adamantylidene, wherein the fluoren-9ylidene substituents may be selected from the group consisting of $C_1$-$C_4$ alkyl, $C_1$-$C_4$ alkoxy, fluoro and chloro.

Preferably, B and B' are each selected from the group consisting of: (i) unsubstituted, mono-, di- and tri-substituted phenyl; (ii) the unsubstituted, mono- and disubstituted heterocyclic aromatic groups pyridyl, furanyl, benzofuran-2-yl, benzofuran-3-yl, thienyl, benzothien-2-yl, benzothien-3-yl, dibenzothienyl, dibenzofuranyl and carbazolyl, each of the phenyl and heterocyclic substituents being selected from the group consisting of morpholino, piperidino, $C_1$-$C_4$ alkyl, $C_1$-$C_4$ alkoxy and halogen, the halogen being fluoro or chloro; (iii) the groups represented by the graphic formula II A, wherein D is carbon and E is oxygen; each $R_8$ is $C_1$-$C_4$ alkyl, $C_1$-$C_4$ alkoxy, hydroxy or halogen, the halogen being chloro or fluoro; $R_9$ and $R_{10}$ are each hydrogen or $C_1$-$C_4$ alkyl; and m is the integer 0, 1 or 2; (iv) $C_1$-$C_4$ alkyl, $C_1$-$C_6$ alkoxy($C_1$-$C_4$)alkyl and $C_3$-$C_6$ cycloalkyl; and (v) the group represented by graphic formula II C, wherein U is hydrogen or methyl, and V is phenyl or mono-substituted phenyl, the phenyl substituent being $C_1$-$C_4$ alkyl, $C_1$-$C_4$ alkoxy or fluoro; or (vi) B and B' taken together form an unsubstituted or mono-substituted fluoren-9-ylidene or a member selected from the group consisting of saturated $C_3$-$C_8$ spiro-monocyclic hydrocarbon rings, saturated $C_7$-$C_{10}$ spiro-bicyclic hydrocarbon rings and saturated $C_7$-$C_{10}$ spiro-tricyclic hydrocarbon rings, said fluoren-9-ylidene substituents being selected from $C_1$-$C_3$ alkyl, $C_1$-$C_3$ alkoxy and fluoro.

More preferably, B and B' are each selected from the group consisting of: (i) unsubstituted, mono- and di-substituted phenyl; (ii) the unsubstituted, mono- and di-substituted heterocyclic aromatic groups pyridyl, benzofuran-2-yl, benzothien-2-yl, dibenzothienyl and dibenzofuranyl, each of the phenyl and heterocyclic substituents being selected from the group consisting of morpholino, piperidino, $C_1$-$C_2$ alkyl and $C_1$-$C_2$ alkoxy; and (iii) the groups represented by graphic formula II A, wherein D is carbon and E is oxygen; each $R_8$ is $C_1$-$C_2$ alkyl, $C_1$-$C_2$ alkoxy or fluoro; $R_9$ and $R_{10}$ are each hydrogen or $C_1$-$C_2$ alkyl; and m is the integer 0, 1 or 2; or (iv) B and B' taken together form fluoren-9-ylidene, bornylidene, norbornylidene, bicyclo[3.3.1]nonan-9-ylidene or adamantylidene. Most preferably, B and B' are each phenyl, methoxy substituted phenyl, morpholino substituted phenyl, dibenzofuran-2-yl, 2,3-dihydrobenzofuran-5-yl or adamantylidene.

Compounds represented by graphic formula I may be prepared by the following steps in Reactions A through D. In Reactions A and B, benzophenones represented by graphic formula V and V A are either purchased or prepared by Friedel-Crafts methods using an appropriately substituted or unsubstituted benzoyl chloride of graphic formula IV and a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

The compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (or VA in Reaction B). R and R' represent potential phenyl substituents.

REACTION A

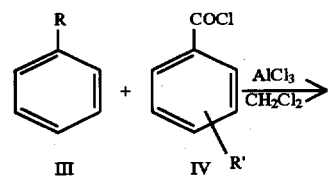

III IV

-continued
REACTION A

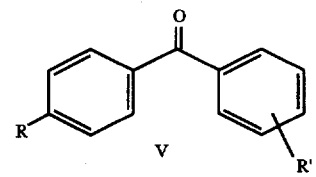

V

In Reaction B, the substituted or unsubstituted ketone represented by graphic formula V A, in which B may represent groups other than phenyl or substituted phenyl, for example, thienyl, furyl or a substituted or unsubstituted naphthalene, is reacted with sodium acetylide in a suitable solvent, such as anhydrous tetrahydrofuran (THF), to form the corresponding propargyl alcohol represented by graphic formula VI. Propargyl alcohols having B or B' groups representing a substituted or unsubstituted benzene or heteroaromatic compound may also be prepared from commercially available ketones or ketones prepared, for example, via reaction of an acyl halide with a substituted or unsubstituted benzene or heteroaromatic compound. Propargyl alcohols having B' groups represented by graphic formula II C may be prepared by the methods described in U.S. Pat. No. 5,274,132, column 2, lines 40 to 68.

REACTION B

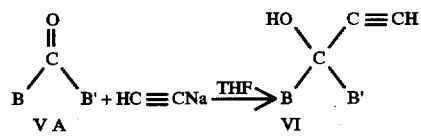

V A VI

In Reaction C, the propargyl alcohol represented by graphic formula VI is coupled with a substituted or unsubstituted 1,3-naphthalene diol, represented by graphic formula VII, under acidic conditions to form the naphthopyran of graphic formula I A.

In order to make the compound represented by graphic formula I B, it is necessary to derivatize, i.e., acylate, benzoylate, etc. . . . , the hydroxyl group on the number 6 carbon atom of the naphthopyran represented by graphic formula I A. This is accomplished by reaction of the hydroxyl group with an acetyl or aroyl halide, chloroformate, isocyanate, etc.

REACTION C

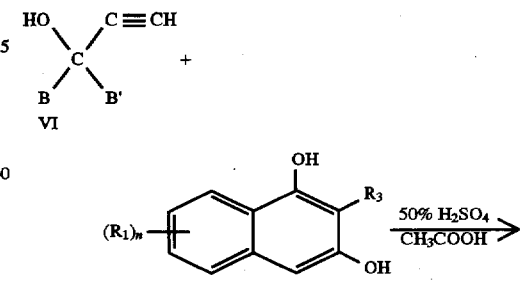

VI VII

-continued
REACTION C

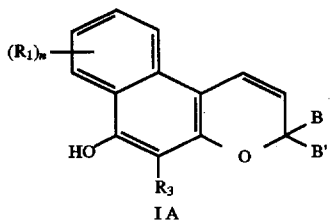

IA

As shown in Reaction D, when $R_2$ in graphic formula I is —H, this substituent can be converted to a variety of different groups by reacting such compound, as represented by graphic formula I A, with acetyl halides, isocyanates or chloroformates. For example, Compound I A may be reacted with acetyl chloride (or other acetyl halides, isocyanates or chloroformates) in the presence of triethylamine in an appropriate solvent, such as methylene chloride, to form compounds represented by the graphic formula I B, in which $R_2$ is an acetyl substituent (or compounds represented by the graphic formula I C, in which $R_2$ is a N-phenyl carbamoyl substituent). Acylating reactions are further described in "Organic Synthesis," Vol. 32, pages 72–77, John Wiley & Sons, Inc., New York, N.Y.

It is contemplated that the organic photochromic naphthopyrans of the present invention may be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which color when activated to an appropriate hue.

Other than in the operating examples, or where otherwise indicated, all numbers expressing wavelengths, quantities of ingredients or reaction conditions used herein are to be understood as modified in all instances by the term "about".

Examples of complementary organic photochromic compounds include other naphthopyrans, benzopyrans, phenanthropyrans, spiro(benzindoline)naphthopyrans, spiro(indoline)benzopyrans, spiro(indoline)naphthopyrans, spiro(indoline)quinopyrans, spiro(indoline)pyrans, spiro(indoline)naphthoxazines, spiro(indoline)pyridobenzoxazines, spiro(benzindoline)pyridobenzoxazines, spiro(benzindoline)naphthoxazines, spiro(indoline)benzoxazines, and mixtures of such photochromic compounds.

Each of the photochromic substances described herein may be used in amounts (or in a ratio) such that an organic

REACTION D

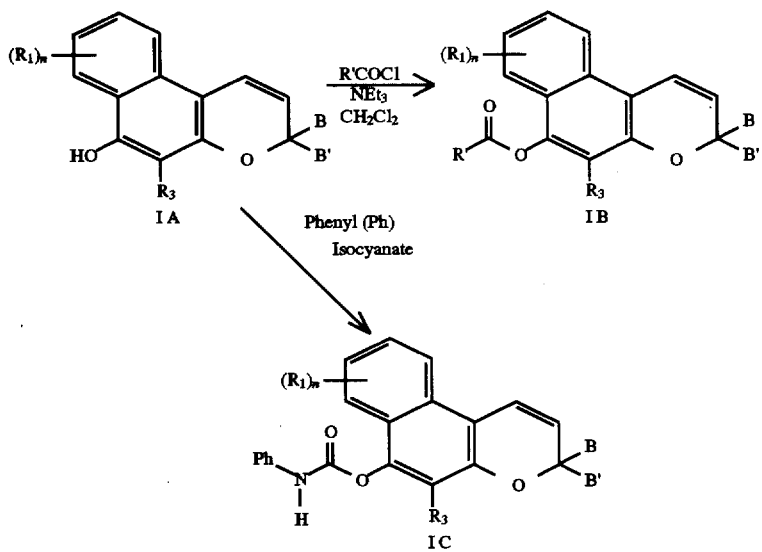

Examples of contemplated naphthopyrans within the scope of the invention are the following:

(a) 3,3-bis(4-methoxyphenyl)-6-acetoxy-3H-naphtho[2,1-b]pyran;

(b) 3,3-diphenyl-6-acetoxy-3H-naphtho[2,1-b]pyran;

(c) 3,3-diphenyl-6-isobutyryloxy-3H-naphtho[2,1-b]pyran;

(d) 3-(4-methoxyphenyl)-3-(benzofur-2-yl)-6-acetoxy-3H-naphtho[2,1-b]pyran;

(e) 3,3'-spiroadamantylene-6-acetoxy-3H-naphtho-[2,1-b]pyran;

(f) 3-(4-methoxyphenyl)-3-(2-methyl-2,3-dihydrobenzofur5-yl)-6-propionyloxy-3H-naphtho[2,1-b]pyran; and (g) 3-(4-methoxyphenyl)-3-(t-butyl)-6-(N-phenylcarbamoyl)oxy-3H-naphth[2,1-b]pyran.

host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., x=X/(X+Y+Z) and y=Y/(X+Y+Z). Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used herein, a near neutral color is one in which the chromaticity coordinate values of "x" and "y" for the color are within the following ranges ($D_{65}$ illuminant): x=0.260 to 0.400, y=0.260 to 0.400 following activation to 40 percent luminous transmittance by exposure to solar radiation (Air Mass 1 or 2).

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from about 0.05 to about 1.0, e.g., from 0.1 to about 0.45, milligrams per square centimeter of surface to which the photochromic substance(s) is incorporated or applied.

The photochromic substances of the present invention may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating placed on the surface of the host material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials which may be used with the photochromic substances or compositions described herein include: polymers, i.e., homopolymers and copolymers, of polyol(allyl carbonate) monomers, diethylene glycol dimethacrylate monomers, diisopropenyl benzene monomers, ethoxylated bisphenol A dimethacrylate monomers, ethylene glycol bismethacrylate monomers, poly (ethylene glycol) bismethacrylate monomers, ethoxylated phenol methacrylate monomers and alkoxylated polyhydric alcohol acrylate monomers, such as ethoxylated trimethylol propane triacrylate monomers; polymers, i.e., homopolymers and copolymers, of polyfunctional, e.g., mono-, di- or multi-functional, acrylate and/or methacrylate monomers, poly($C_1$-$C_{12}$ alkyl methacrylates), such as poly(methyl methacrylate), poly(oxyalkylene dimethacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, poly(alpha methylstyrene), copoly(styrene-methyl methacrylate), copoly (styreneacrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol methacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic naphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66. Specifically contemplated are optical resins sold by PPG Industries, Inc. under the designation CR-307 and CR-407.

The present invention is more particularly described in the following examples which are intended as illustrative only, since numerous modifications and variations therein will be apparent to those skilled in the art.

EXAMPLE I

STEP I 4,4'-Dimethoxybenzophenone (0.27 mole) was dissolved in a reaction flask containing 200 milliliters (ml) of anhydrous tetrahydrofuran saturated with acetylene and stirred at room temperature. An 18 weight percent suspension of sodium acetylide in xylene/mineral oil (0.3 mole of sodium acetylide) was added to the reaction flask and the mixture was stirred. After stirring 16 hours at room temperature under a nitrogen atmosphere, the contents of the reaction flask was added to a 5 weight percent aqueous hydrochloric acid and ice mixture. The resulting mixture was extracted with diethyl ether. The organic layer was separated, washed and dried over anhydrous sodium sulfate. The solvents, diethyl ether and tetrahydrofuran, were removed under vacuum to yield an oily product containing 1,1-bis(4-methoxyphenyl)-2-propyn-1-ol, which was crystallized from diethyl ether:hexane mixture. The recovered product (about 60 grams (g)) had a melting point of 83°–84° C. A nuclear magnetic resonance (NMR) showed the product to have a structure consistent with 1,1-bis(4-methoxyphenyl)-2-propyn-1-ol.

STEP 2

1,1-Bis(4-methoxyphenyl)-2-propyn-1-ol (8 gm, 0.025 mole) from Step 1 and 1,3-dihydroxynaphthalene (5 gm., 0.031 mole) were added to a reaction flask containing 50 ml of acetic acid and stirred at room temperature. 50% Sulfuric acid (0.5 ml) was slowly added and the reaction mixture was stirred for five hours. Afterwards, the reaction mixture was filtered and the solid was washed with small amount of acetic acid. A nuclear magnetic resonance (NMR) spectrum showed the crystalline product to have a structure consistent with 3,3-bis(4-methoxyphenyl)-6-hydroxy-3H-naphtho[2,1-b]pyran.

STEP 3

3,3-Bis(4-methoxyphenyl)-6-hydroxy-3H-naphtho[2,1-b]pyran (2 grams) prepared in Step 2 and triethylamine (2 grams) were added to a reaction flask containing 50 ml of anhydrous methylene chloride and stirred. Acetyl chloride (2 grams) was added to the reaction flask and the reaction mixture was stirred for 1 hour. Distilled water (50 ml) was added to the reaction flask and the reaction mixture was stirred for another half hour. Afterwards, the organic layer was separated, washed and dried over anhydrous sodium sulfate. Evaporation of solvent resulted in an oily residue that was crystallized from a 1:1 hexane:diethyl ether mixture. The solid was suction filtered, washed with hexane, and air dried. The resulting product had a melting point of 129°–130° C. A nuclear magnetic resonance (NMR) spectrum showed the product to have a structure consistent with 3,3-bis(4-methoxyphenyl)6-acetoxy-3H-naphtho[2,1-b]pyran.

EXAMPLE 2

The procedure of Example 1 was followed except that in Step 2, 1,1-diphenyl-2-propyn-1-ol was used in place of 1,1-bis(4-methoxyphenyl)-2-propyn-1-ol. The resulting product had a melting point of 160°–162° C. A nuclear magnetic resonance (NMR) spectrum showed the product to have a structure consistent with 3,3-diphenyl-6-acetoxy-3Hnaphtho[2,1-b]pyran.

EXAMPLE 3

STEP 1

The procedure of Step 2 of Example 1 was followed except that 1,1-diphenyl-2-propyn-1-ol was used in place of 1,1-bis(4-methoxyphenyl)-2-propyn-1-ol to produce 3,3-diphenyl-6-hydroxy-3H-naphtho[2,1-b]pyran.

STEP 2

The procedure of Step 3 of Example 1 was followed except that isobutyryl chloride was used in place of acetyl chloride. The resulting product had a melting point of 139°–140° C. A nuclear magnetic resonance (NMR) spectrum showed the product to have a structure consistent with 3,3-diphenyl-6-isobutyryloxy-3H-naphtho[2,1-b]pyran.

COMPARATIVE EXAMPLES

The comparative examples tested were identified as 3,3-dianisyl-6-morpholino-3H-naphtho[2,1-b]pyran in Example 3 of WO 94/22850, herein designated Comparative Example 1; and 3,3-dianisyl-6-methoxy-3H-naphtho[2,1-b]pyran in Example 1 of WO 95/05371, herein designated Comparative Example 2.

EXAMPLE 4

PART A

Testing was done with the photochromic naphthopyrans of the Examples and Comparative Examples incorporated into polymeric samples by the following method. The quantity of naphthopyran calculated to yield a 1.5 times $10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The naphthopyran was dissolved into the monomer blend by stirring and gentle heating, if necessary. After a clear solution was obtained, it was poured into a flat sheet mold having the interior dimensions of 2.2 mm×6 inches (15.24 cm) ×6 inches (15.24 cm). The mold was sealed and placed in a horizontal air flow, programmable oven set to increase the temperature from 40° C. to 95° C. over a 5 hour interval, hold the temperature at 95° C. for 3 hours and then lower it to 60° C. for at least 2 hours before the end of the curing cycle. After the mold was opened, the polymer sheet was cut using a diamond blade saw into 2 inch (5.1 centimeters) test squares.

Part B

The photochromic test squares prepared in Part A were tested for percent luminous transmittance (Y) and color (CIE 1976 L* a* b* Scale) in a Spectrogard® II spectrophotometer. A $D_{65}$ illuminant was used and measurements were made from a 10° observation angle. Prior to testing in the spectrophotometer, the photochromic test squares were exposed to 365 nanometer ultraviolet light for about 15 minutes to activate the photochromic compounds and then placed into a 76° C oven for about 15 minutes to bleach or inactivate the photochromic compounds. The test squares were then cooled to room temperature, exposed to fluorescent room lighting for at least 2 hours and then kept covered for at least 2 hours prior to testing in the spectrophotometer. After calibrating the spectrophotometer with a standard test square, i.e., one having known values, the percent luminous transmittance and the color of the test squares of Examples 1-3 and Comparative Examples 1 and 2 were determined. The results for Y, a* and b* are tabulated in Table 1.

TABLE 1

| Identification | Y | a* | b* |
| --- | --- | --- | --- |
| Example 1 | 87.7 | 0.1 | 5.9 |
| Example 2 | 89.5 | −0.6 | 3.1 |
| Example 3 | 90.5 | −0.3 | 2.0 |
| Comparative Example 1 | 86.6 | 0.1 | 9.6 |
| Comparative Example 2 | 78.5 | 2.8 | 29.6 |

The results of Table 1 show that the test squares prepared with Examples 1, 2 and 3 as compared to the test squares prepared with Comparative Examples 1 and 2, demonstrated, in the unactivated state, higher percent luminous transmittance values (Y); lower values for (b*), i.e., less yellowness on the yellow-blue axis; and 2 of the 3 examples showed negative values for (a*), i.e., more greenness on the red-green axis.

Although the present invention has been described with reference to the specific details of particular embodiments thereof, it is not intended that such details be regarded as limitations upon the scope of the invention except as and to the extent that they are included in the accompanying claims.

What is claimed is:

1. A naphthopyran compound represented by the following graphic formula:

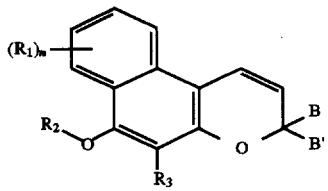

wherein:

(a) $R_1$ is $C_1$-$C_6$ alkyl, $C_5$-$C_7$ cycloalkyl, chloro, fluoro, the group, —$OR_4$, or the group, —C(O)W, W being $C_1$-$C_6$ alkyl, —$OR_5$ or —N($R_6$)$R_7$, wherein $R_4$ is hydrogen, allyl, $C_1$-$C_6$ alkyl, phenyl, $C_1$-$C_6$ monoalkyl substituted phenyl, $C_1$-$C_6$ monoalkoxy substituted phenyl, phenyl($C_1$-$C_3$)alkyl, $C_1$-$C_6$ monoalkyl substituted phenyl($C_1$-$C_3$)alkyl, $C_1$-$C_6$ monoalkoxy substituted phenyl($C_1$-$C_3$)alkyl, $C_1$-$C_6$ alkoxy($C_2$-$C_4$)alkyl, $C_1$-$C_6$ monofluoroalkyl, $C_1$-$C_6$ monochloroalkyl, $C_1$-$C_6$ alkylcarbonyl, monochloro($C_1$-$C_6$)alkylcarbonyl, monofluoro($C_1$-$C_6$)alkylcarbonyl, $C_1$-$C_6$ monoalkylaminocarbonyl, mono- or di-substituted arylcarbonyl, said aryl group being phenyl or naphthyl, wherein $R_5$ is hydrogen, allyl, $C_1$-$C_6$ alkyl, phenyl, $C_1$-$C_6$ monoalkyl substituted phenyl, $C_1$-$C_6$ monoalkoxy substituted phenyl, phenyl($C_1$-$C_3$)alkyl, $C_1$-$C_6$ monoalkyl substituted phenyl($C_1$-$C_3$)alkyl, $C_1$-$C_6$ monoalkoxy substituted phenyl($C_1$-$C_3$)alkyl, $C_1$-$C_6$ alkoxy($C_2$-$C_4$)alkyl, $C_1$-$C_6$ monofluoroalkyl or $C_1$-$C_6$ monochloroalkyl, and wherein $R_6$ and $R_7$ are each selected from the group consisting of hydrogen, $C_1$-$C_6$ alkyl, $C_5$-$C_7$ cycloalkyl, phenyl, mono- substituted and di-substituted phenyl, or $R_6$ and $R_7$ together with the attached nitrogen atom form an unsubstituted, mono- substituted or di-substituted heterocyclic ring selected from the group consisting of indolinyl, morpholino, piperidino, 1-pyrrolidyl, 1-pyrrolinyl, 1-imidazolidyl, 2-imidazolin-1-yl, 2-pyrazolidyl and 1-piperazinyl, said phenyl, naphthyl and heterocyclic ring substituents being $C_1$-$C_6$ alkyl or $C_1$-$C_6$ alkoxy, and n is the integer 0, 1, 2 or 3;

(b) $R_2$ is hydrogen, or the group, —C(O)X, wherein X is hydrogen, $C_1$-$C_6$ alkyl, $C_1$-$C_6$ alkoxy, $C_1$-$C_6$ monofluoroalkyl, $C_1$-$C_6$ monochloroalkyl, phenyl($C_1$-$C_3$)alkyl, mono($C_1$-$C_6$)alkyl substituted phenyl($C_1$-$C_3$) alkyl, mono($C_1$-$C_6$)alkoxy substituted phenyl($C_1$-$C_3$) alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ alkylamino, allyl, or the unsubstituted, mono-substituted or di-substituted member selected from the group consisting of phenyl, naphthyl, phenoxy and phenylamino, said group substituents being $C_1$-$C_6$ alkyl or $C_1$-$C_6$ alkoxy;

(c) $R_3$ is hydrogen or a $C_1$-$C_6$ alkyl; and (d) B and B' are each selected from the group consisting of:

(i) unsubstituted, mono-, di- and tri-substituted phenyl;

(ii) the unsubstituted, mono- and di-substituted heterocyclic aromatic groups pyridyl, benzofuran-2-yl, benzofuran-3-yl, benzothien-2-yl, benzothien-3-yl, dibenzothienyl, dibenzofuranyl, and carbazolyl, said aryl and heterocyclic substituents described in (i) and (ii) being selected from the group consisting of hydroxy, amino, $C_1$-$C_6$ monoalkylamino, $C_1$-$C_6$ dialkylamino, morpholino, piperidino, 1-indolinyl, pyrrolidyl, 1-imidazolidyl, 2-imidazolin-1-yl, 2-pyrazolidyl, pyrazolinyl, 1-piperazinyl, $C_1$-$C_6$ alkyl, $C_1$-$C_6$ haloalkyl, $C_1$-$C_6$ alkoxy, mono($C_1$-$C_6$) alkoxy($C_1$-$C_4$)alkyl, acryloxy, methacryloxy and halogen, said halogen or (halo) group being fluoro or chloro; and (iii) $C_1$-$C_6$ alkyl, $C_1$-$C_6$ haloalkyl, $C_1$-$C_6$ alkoxy($C_1$-$C_4$)alkyl, $C_3$-$C_6$ cycloalkyl, mono($C_1$-$C_6$) alkoxy ($C_3$-$C_6$)cycloalkyl, mono($C_1$-$C_6$)alkyl($C_3$-$C_6$) cycloalkyl, and halo($C_3$-$C_6$)cycloalkyl, each of said halo groups being fluoro or chloro; or (iv) B and B' taken together form a member selected from the group consisting of saturated $C_7$-$C_{12}$ spiro-bicyclic hydrocarbon rings, and saturated $C_7$-$C_{12}$ spiro-tricyclic hydrocarbon rings.

2. The naphthopyran of claim 1 wherein:
(a) $R_1$ is a $C_1$-$C_4$ alkyl, or the group, —$OR_4$, wherein $R_4$ is hydrogen, $C_1$-$C_4$ alkyl, phenyl, $C_1$-$C_4$ monoalkyl substituted phenyl, $C_1$-$C_4$ monoalkoxy substituted phenyl, phenyl($C_1$-$C_3$)alkyl, $C_1$-$C_4$ monoalkyl substituted phenyl($C_1$-$C_3$)alkyl, $C_1$-$C_4$ monoalkoxy substituted phenyl($C_1$-$C_3$)alkyl, $C_1$-$C_4$ alkoxy($C_2$-$C_4$)alkyl, $C_1$-$C_4$ monofluoroalkyl, $C_1$-$C_4$ monochloroalkyl or $C_1$-$C_4$ alkylcarbonyl, and n is the integer 0, 1 or 2;
(b) $R_2$ is hydrogen, or the group, —C(O)X, wherein X is hydrogen, $C_1$-$C_4$ alkyl, $C_1$-$C_4$ alkoxy, $C_1$-$C_4$ monofluoroalkyl, $C_1$-$C_4$ monochloroalkyl, phenyl($C_1$-$C_3$)alkyl, mono($C_1$-$C_4$)alkyl substituted phenyl($C_1$-$C_3$) alkyl, mono($C_1$-$C_4$)alkoxy substituted phenyl($C_1$-$C_3$) alkyl, $C_1$-$C_4$ alkoxy($C_2$-$C_4$)alkyl, $C_3$-$C_7$ cycloalkyl, phenyl, mono($C_1$-$C_4$)alkyl substituted phenyl, mono ($C_1$-$C_4$)alkoxy substituted phenyl, phenoxy, mono($C_1$-$C_4$)alkyl substituted phenoxy, mono($C_1$-$C_4$)alkoxy substituted phenoxy, $C_1$-$C_4$ alkylamino, phenylamino, mono($C_1$-$C_4$)alkyl substituted phenylamino, or mono ($C_1$-$C_4$)alkoxy substituted phenylamino;
(c) $R_3$ is hydrogen or a $C_1$-$C_4$ alkyl; and
(d) B and B' are each selected from the group consisting of:
  (i) unsubstituted, mono-, di- and tri-substituted phenyl;
  (ii) the unsubstituted, mono- and di-substituted heterocyclic aromatic groups pyridyl, benzofuran-2-yl, benzofuran-3-yl, benzothien-2-yl, benzothien-3-yl, dibenzothienyl, dibenzofuranyl, and carbazolyl, each of said aryl and heterocyclic substituents in this part (i) and (ii) being selected from the group consisting of morpholino, piperidino, $C_1$-$C_4$ alkyl, $C_1$-$C_4$ alkoxy and halogen, said halogen being fluoro or chloro; and
  (iii) $C_1$-$C_4$ alkyl, $C_1$-$C_6$ alkoxy($C_1$-$C_4$)alkyl, and $C_3$-$C_6$ cycloalkyl; or
  (iv) B and B' taken together form a member selected from the group consisting of saturated $C_7$-$C_1$O spirobicyclic hydrocarbon rings, and saturated $C_7$-$C_{10}$ spiro-tricyclic hydrocarbon rings.

3. The naphthopyran of claim 2 wherein:
(a) $R_1$ is a $C_1$-$C_3$ alkyl, or the group, —$OR_4$, wherein $R_4$ is hydrogen, $C_1$-$C_3$ alkyl, phenyl, $C_1$-$C_3$ monoalkyl substituted phenyl, $C_1$-$C_3$ monoalkoxy substituted phenyl, $C_1$-$C_3$ alkoxy($C_2$-$C_4$)alkyl, $C_1$-$C_3$ monofluoroalkyl or $C_1$-$C_3$ alkylcarbonyl, and n is the integer 0, 1 or 2;
(b) $R_2$ is hydrogen, or the group, —C(O)X, wherein X is hydrogen, $C_1$-$C_3$ alkyl, $C_1$-$C_3$ alkoxy, $C_1$-$C_3$ monofluoroalkyl, phenyl, mono($C_1$-$C_3$)alkyl substituted phenyl, mono($C_1$-$C_3$)alkoxy substituted phenyl, phenoxy, mono($C_1$-$C_3$)alkyl substituted phenoxy, mono($C_1$-$C_3$)alkoxy substituted phenoxy, $C_1$-$C_3$ alkylamino, phenylamino, mono($C_1$-$C_3$)alkyl substituted phenylamino, or mono($C_1$-$C_3$)alkoxy substituted phenylamino;
(c) $R_3$ is hydrogen or a $C_1$-$C_3$ alkyl; and
(d) B and B' are each selected from the group consisting of:
  (i) unsubstituted, mono-, and di-substituted phenyl; and
  (ii) the unsubstituted, mono- and di-substituted heterocyclic aromatic groups pyridyl, benzofuran-2-yl, benzothien-2-yl, dibenzothienyl and dibenzofuranyl, each of said phenyl and heterocyclic substituents in parts (i) and (ii) being selected from the group consisting of morpholino, piperidino, $C_1$-$C_2$ alkyl and $C_1$-$C_2$ alkoxy; or
  (iii) B and B' taken together form bornylidene, norbornylidene, bicyclo [3.3.1]nonan-9-ylidene or adamantylidene.

4. The naphthopyran of claim 3 wherein:
(a) $R_1$ is a $C_1$-$C_2$ alkyl or the group, —$OR_4$, wherein $R_4$ is a $C_1$-$C_2$ alkyl, and n is the integer 0 or 1;
(b) $R_2$ is hydrogen or the group, —C(O)X, wherein X is $C_1$-$C_2$ alkyl, $C_1$-$C_2$ alkoxy or $C_1$-$C_2$ alkylamino;
(c) $R_3$ is hydrogen; and
(d) B and B' are each phenyl, methoxy substituted phenyl, morpholino substituted phenyl, dibenzofuran-2-yl or adamantylidene.

5. A naphthopyran compound selected from the group consisting of:
(a) 3,3-bis(4-methoxyphenyl)-6-acetoxy-3H-naphtho[2,1-b]pyran;
(b) 3,3-diphenyl-6-acetoxy-3H-naphtho[2,1-b]pyran;
(c) 3,3-diphenyl-6-isobutyryloxy-3H-naphtho[2,1-b]pyran;
(d) 3-(4-methoxyphenyl)-3-(benzofur-2-yl)-6-acetoxy3H-naphtho[2,1-b]pyran;
(e) 3,3'-spiroadamantylene-6-acetoxy-3H-naphtho-[2,1-b]pyran; and
(f) 3-(4-methoxyphenyl)-3-(t-butyl)-6-(N-phenylcarbamoyl)oxy-3H-naphth[2,1-b]pyran.

6. A photochromic article comprising a polymeric organic host material and a photochromic amount of a naphthopyran compound of claim 1.

7. The photochromic article of claim 6 wherein the polymeric organic host material is selected from the group consisting of polyacrylates, polymethacrylates, poly($C_1$-$C_{12}$ alkyl methacrylates), polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly (styreneacrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

8. A photochromic article comprising a polymeric organic host material and a photochromic amount of a naphthopyran compound of claim 2.

9. The photochromic article of claim 8 wherein the polymeric organic host material is selected from the group consisting of polyacrylates, polymethacrylates, poly($C_1$-$C_{12}$ alkyl methacrylates), polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly (styreneacrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

10. The photochromic article of claim 9 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, diisopropenyl benzene monomers, and ethoxylated trimethylol propane triacrylate monomers.

11. The photochromic article of claim 10 wherein the photochromic compound is present in an amount of from about 0.05 to 1.0 milligram per square centimeter of organic host material surface to which the photochromic substance(s) is incorporated or applied.

12. The photochromic article of claim 11 wherein the article is a lens.

13. A photochromic article comprising a is photochromic amount of the naphthopyran compound of claim 3 and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, diisopropenyl benzene monomers, and ethoxylated trimethylol propane triacrylate monomers.

14. A photochromic article comprising a photochromic amount of the naphthopyran compound of claim 4 and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, diisopropenyl benzene monomers, and ethoxylated trimethylol propane triacrylate monomers.

15. A photochromic article comprising, in combination, a solid transparent polymeric organic host material, and a photochromic amount of each of (a) at least one naphthopyran compound of claim 1, and (b) at least one other organic photochromic compound having at least one activated absorption maxima within the range of between about 400 and 700 nanometers.

16. The photochromic article of claim 15 wherein the polymeric organic host material is selected from the group consisting of polyacrylates, polymethacrylates, poly($C_1$-$C_{12}$ alkyl methacrylates), polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly (styreneacrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

17. The photochromic article of claim 16 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, diisopropenyl benzene monomers, and ethoxylated trimethylol propane triacrylate monomers.

18. The photochromic article of claim 15 wherein the organic photochromic compound (b) is selected from the group consisting of naphthopyrans, benzopyrans, phenanthropyrans, spiro(benzindoline)naphthopyrans, spiro (indoline)benzopyrans, spiro(indoline)naphthopyrans, spiro (indoline)quinopyrans, spiro(indoline)pyrans, spiro (indoline)naphthoxazines, spiro(indoline) pyridobenzoxazines, spiro(benzindoline) pyridobenzoxazines, spiro(benzindoline)naphthoxazines, spiro(indoline)benzoxazines and mixtures of such photochromic compounds.

19. The photochromic article of claim 18 wherein the photochromic compound is present in an amount of from about 0.05 to 1.0 milligram per square centimeter of organic host material surface to which the photochromic substance(s) is incorporated or applied.

20. The photochromic article of claim 19 wherein the article is a lens.

* * * * *

UNITED STATES PATENT AND TRADEMARK OFFICE
CERTIFICATE OF CORRECTION

PATENT NO. : 5,744,070
DATED : April 28, 1998
INVENTOR(S) : Anil Kumar

It is certified that error appears in the above-indentified patent and that said Letters Patent is hereby corrected as shown below:

Column 15, line 38, claim 2,

"$C_7-C_1O$" should be --$C_7-C_{10}$--.

Column 17, line 21, claim 13,

"comprising a is" should be --comprising a--.

Signed and Sealed this

Eighth Day of September, 1998

Attest:

BRUCE LEHMAN

*Attesting Officer*     *Commissioner of Patents and Trademarks*